(12) United States Patent
Cho (10) Patent No.: US 8,263,001 B2
(45) Date of Patent: Sep. 11, 2012

(54) INTEGRATED BIO-CHIP, METHOD OF FABRICATING THE INTEGRATED BIO-CHIP, AND APPARATUS FOR DETECTING BIO-MATERIAL

(75) Inventor: Seong-ho Cho, Gwacheon-si (KR)

(73) Assignee: Samsung Electronics Co., Ltd., Maetan-dong, Yeongtong-gu, Suwon-si, Gyeonggi-do (KR)

( * ) Notice: Subject to any disclaimer, the term of this patent is extended or adjusted under 35 U.S.C. 154(b) by 198 days.

(21) Appl. No.: 12/609,253

(22) Filed: Oct. 30, 2009

(65) Prior Publication Data
US 2010/0111762 A1 May 6, 2010

(30) Foreign Application Priority Data
Oct. 31, 2008 (KR) .................. 10-2008-0107965

(51) Int. Cl.
*G01N 21/00* (2006.01)
*G02B 6/00* (2006.01)
*F21V 9/16* (2006.01)
*C12Q 1/68* (2006.01)
*G01J 3/30* (2006.01)

(52) U.S. Cl. .............. 422/82.11; 422/82.08; 422/82.09; 435/6.1; 435/7.1; 435/287.2; 356/317; 385/12; 250/458.1

(58) Field of Classification Search .................. None
See application file for complete search history.

(56) References Cited

U.S. PATENT DOCUMENTS

| | | | |
|---|---|---|---|
| 5,936,730 A | 8/1999 | Foley et al. | |
| 6,197,503 B1* | 3/2001 | Vo-Dinh et al. | 435/6.11 |
| 7,384,797 B1* | 6/2008 | Blair | 436/524 |
| 2001/0023077 A1* | 9/2001 | Erb et al. | 436/518 |
| 2002/0191182 A1* | 12/2002 | Tsipouras et al. | 356/317 |
| 2003/0092034 A1* | 5/2003 | Cooper et al. | 435/6 |
| 2004/0234417 A1 | 11/2004 | Schienle et al. | |
| 2007/0117217 A1* | 5/2007 | Lal et al. | 436/513 |

FOREIGN PATENT DOCUMENTS

| | | |
|---|---|---|
| JP | 2002-350349 | 12/2002 |
| JP | 2004-257737 A | 9/2004 |
| JP | 2005-181352 A | 7/2005 |
| JP | 2008-003061 | 1/2008 |
| KR | 1020000041459 A | 7/2000 |

OTHER PUBLICATIONS

Bhaskar Mitra, et al., "Microfluidic discharge-based optical sources for detection of biochemicals", The Royal Society of Chemistry, Lab Chip, 2006, 6, pp. 60-65.
Korean Office Action with English Translation for Application No. 10-2008-0107965 dated Jan. 27, 2011.

* cited by examiner

*Primary Examiner* — Neil N Turk (57) ABSTRACT

An integrated bio-chip includes a substrate and one or more excitation light absorbing waveguides disposed in the substrate. The substrate includes one or more reaction regions on which samples are disposed. An end portion of each of the one or more excitation light absorbing waveguides is exposed from the substrate at an upper surface thereof, another end portion of each of the one or more excitation light absorbing waveguides is exposed from the substrate at a lower surface thereof, and the one or more reaction regions are disposed at a upper surface of the substrate. The one or more excitation light absorbing waveguides absorbs excitation light incident to the samples, and transmits fluorescent light emitted from the samples.

31 Claims, 7 Drawing Sheets

INTEGRATED BIO-CHIP, METHOD OF FABRICATING THE INTEGRATED BIO-CHIP, AND APPARATUS FOR DETECTING BIO-MATERIAL

CROSS-REFERENCE TO RELATED APPLICATION

This application claims priority to Korean Patent Application No. 10-2008-0107965, filed on Oct. 31, 2008, and all the benefits accruing therefrom under 35 U.S.C. §119, the content of which in its entirety is herein incorporated by reference.

BACKGROUND

1) Field

The general inventive concept relates to an integrated bio-chip, a method of fabricating the same, and an apparatus for detecting bio-material. More particularly, the general inventive concept relates to an integrated bio-chip including an excitation light absorption waveguide used for spectroscopically detecting a sample, a method of fabricating the integrated bio-chip and an apparatus for detecting bio-material using the integrated bio-chip.

2) Description of the Related Art

Bio-chips typically have a structure in which cells, which include biogenic organic materials such as nucleotide or protein, are arranged on a substrate in a matrix shape. Bio-materials, fixed on the substrate of the bio-chip, operate as biological receptors for target bio-materials.

Bio-chips detect the target bio-materials via interaction between bio-materials, such as a hybridization reaction of a nucleotide, or an antigen-antibody interaction, for example. The bio-chips may be used to research functions of genes, to search for illness-related genes, to analyze gene expression or to analyze protein distribution by detecting the bio-materials such as nucleotide or protein having a specific sequence.

The interaction between the bio-materials may be detected using a fluorescence detection method. More specifically, the fluorescence detection method is a spectroscopic method of detecting fluorescent images by irradiating a predetermined excitation light on fluorescent materials tagged on the bio-materials. The fluorescent images are detected using an optical scanning apparatus such as a photo-multiplier-tube ("PMT"), a charge-coupled device ("CCD") scanner or a complementary metal oxide semiconductor ("CMOS") image sensor ("CIS") scanner, for example.

The fluorescence detected by irradiating the predetermined excitation light onto the fluorescent material tagged on the bio-materials is much weaker than the irradiated excitation light, and thus, it is desired to remove the excitation light. In addition, current detection apparatuses use a scanner-type photodetector that is complex and expensive, and thus, there is a need for a compact bio-chip and a detection apparatus having the same.

SUMMARY

The general inventive concept provides an integrated bio-chip that effectively removes excitation lights for fluorescence excitation in samples such as bio-materials, a method of fabricating the integrated bio-chip and an apparatus for detecting bio-material.

According to an aspect of the general inventive concept, there is provided an integrated bio-chip including a substrate and one or more excitation light absorbing waveguides disposed in the substrate. The substrate includes one or more reaction regions on which samples are disposed. A first end portion of each of the one or more excitation light absorbing waveguides is exposed from the substrate at an upper surface thereof, a second end portion of each of the one or more excitation light absorbing waveguides is exposed from the substrate at a lower surface thereof, and the one or more reaction regions are disposed at the upper surface of the substrate. The one or more excitation light absorbing waveguides absorbs excitation light which excites the samples, and transmits fluorescent light emitted from the samples.

Each of the one or more excitation light absorbing waveguides may include a color filter core which transmits the fluorescent light emitted from the samples and absorbs the excitation light which excites the samples.

A refractive index of the color filter core may be greater than a refractive index of the substrate surrounding the color filter core.

Each of the one or more excitation light absorbing waveguide may further include a clad layer disposed around the color filter core, and the clad layer may have a refractive index that is less than the refractive index of the color filter core.

The clad layer may have a single layered structure or a multi-layered structure.

A transverse cross-section of the color filter core may be a circle or a polygon.

Surfaces of the one or more reaction regions may be treated so that the samples may be attached to thereto.

The surfaces of the one or more reaction regions have hydrophilic properties, and non-reaction regions surrounding the surfaces of the one or more reaction regions have hydrophobic properties.

The integrated bio-chip may further include one or more micro lenses disposed on the one or more reaction regions, and the one or more micro lenses may condense the fluorescent light emitted from the samples.

The one or more micro lenses may be concave or convex.

The integrated bio-chip may further include one or more anti-reflection layers disposed on the one or more reaction regions, and the one or more anti-reflection layers may transmit the fluorescent light emitted from the samples.

The integrated bio-chip may further include a photodetector disposed at the lower surface side of the substrate, which is opposite to the upper surface, thereof, and the photodetector may either be disposed adjacent to and separate from the substrate or in contact with the substrate.

Pixels of the photodetector may correspond to the one or more reaction regions in a one-to-one correspondence or a one-to-many correspondence.

The photodetector may include a photomultiplier tube ("PMT"), a charge coupled device ("CCD") or a complementary metal oxide semiconductor ("CMOS") image sensor image sensor ("CIS").

According to another aspect of the general inventive concept disclosed herein, a method of fabricating an integrated bio-chip includes: forming one or more penetration holes in a substrate; forming one or more excitation light absorbing waveguides in the one or more penetration holes; and treating a surface of the substrate in which the one or more penetration holes are formed such that samples are attachable to reaction regions at which the one or more excitation light absorbing waveguides are formed.

The one or more penetration holes may be through vias formed in the substrate, and the substrate may be a semiconductor material, a dielectric material, a metal material or a polymer material.

The forming of the one or more excitation light absorbing waveguides may include forming a color filter core by disposing color filter material in each of the one or more penetration holes.

The forming of the one or more excitation light absorbing waveguides may include forming a clad layer on an inner wall of each of the one or more penetration holes.

The forming of the clad layer may include oxidizing the inner wall of each of the one or more penetration holes to reduce a refractive index of the inner wall of each of the one or more penetration holes.

The forming of the clad layer may include diffusing a dopant onto the inner wall of each of the one or more penetration holes to reduce the refractive index of the inner wall of each of the one or more penetration holes.

The forming of the clad layer may include applying a material having a low refractive index, relative to a refractive index of the color filter core, onto the inner wall of each of the one or more penetration holes.

The treating of the surface of the substrate onto which the one or more penetration holes are formed may include treating portions of the substrate at which the one or more excitation light absorbing waveguides are formed so that the portions have a hydrophilic property.

The method may further include forming an anti-reflection layer on the portions of the substrate where the one or more excitation light absorbing waveguides are formed.

The method may further include forming one or more micro lenses on the portions of the substrate where the one or more excitation light absorbing waveguides are formed.

The method may further include performing a back-lap process to polish the lower surface of the substrate to a depth that is greater than a length of the one or more penetration holes.

According to another aspect of the general inventive concept disclosed herein, an apparatus for detecting bio-material using an integrated bio-chip is provided. The integrated bio-chip includes a substrate including one or more reaction regions on which samples are disposed and one or more excitation light absorbing waveguides disposed in the substrate. The apparatus includes: an illuminating optical system which irradiates excitation light onto the integrated bio-chip; a stage detachably mounted to the integrated bio-chip; and a photodetector which detects fluorescent light emitted from the integrated bio-chip. A first end portion of each of the one or more excitation light absorbing waveguides is exposed from the substrate at an upper surface thereof, a second end portion of each of the one or more excitation light absorbing waveguides is exposed from the substrate at a lower surface thereof, the one or more reaction regions are disposed at the upper surface of the substrate, the one or more excitation light absorbing waveguides absorbs excitation light which excites the samples, and the one or more excitation light absorbing waveguides transmits the fluorescent light emitted from the samples.

The photodetector may be disposed on the stage.

The photodetector may be disposed either spaced apart from and adjacent to the integrated bio-chip or in contact with the integrated bio-chip.

The apparatus may further include a detecting optical system which transfers the fluorescent light emitted from the integrated bio-chip to the photodetector.

Pixels of the photodetector may correspond to the one or more reaction regions in either a one-to-one correspondence or a one-to-many correspondence.

The photodetector may includes a photomultiplier tube, a charge coupled device and a complementary metal oxide semiconductor image sensor.

BRIEF DESCRIPTION OF THE DRAWINGS

The above and/or other aspects will become more readily apparent and more readily appreciated from the following description of the embodiments, taken in conjunction with the accompanying drawings, in which.

DETAILED DESCRIPTION

The invention now will be described more fully hereinafter with reference to the accompanying drawings, in which various embodiments are shown. This invention may, however, be embodied in many different forms, and should not be construed as limited to the embodiments set forth herein. Rather, these embodiments are provided so that this disclosure will be thorough and complete, and will fully convey the scope of the invention to those skilled in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

The embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

Hereinafter, embodiments of the general inventive concept will be described in further detail with reference to the accompanying drawings.

Figure 1:
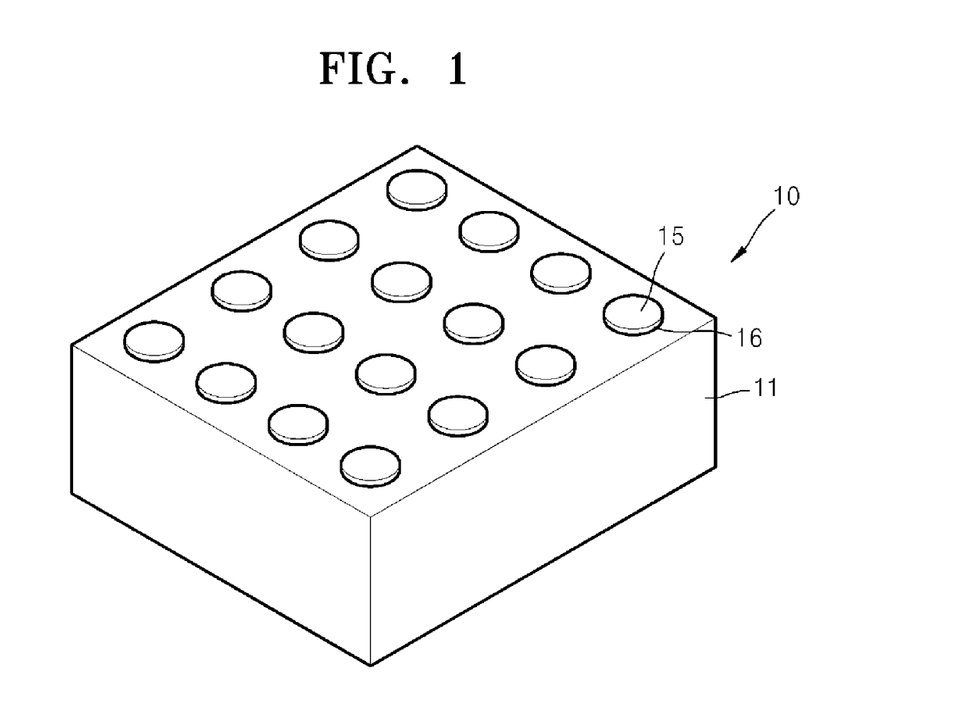
FIG. 1 is a perspective view of an integrated bio-chip according to an embodiment.
Figure 2:
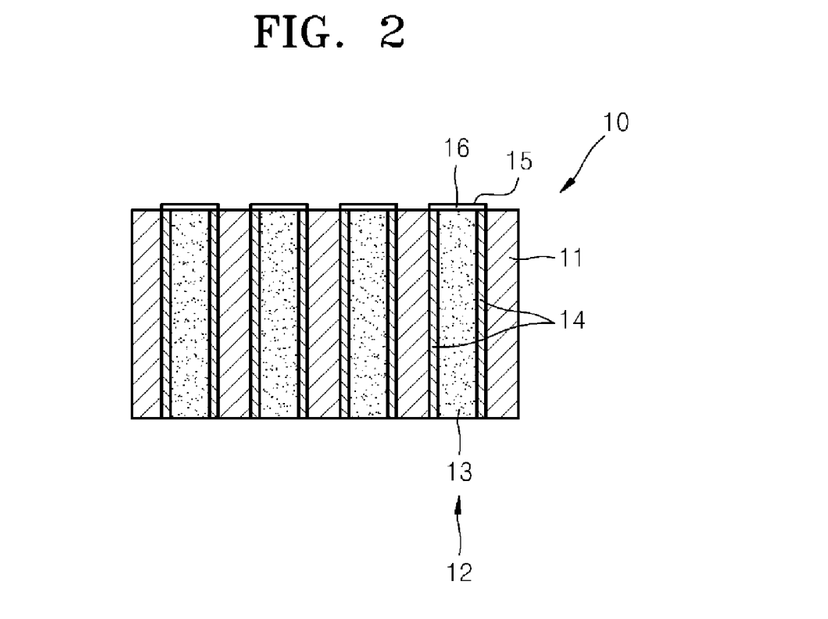
FIG. 2 is a partial cross-sectional view of the integrated bio-chip of FIG. 1.
Figure 3:
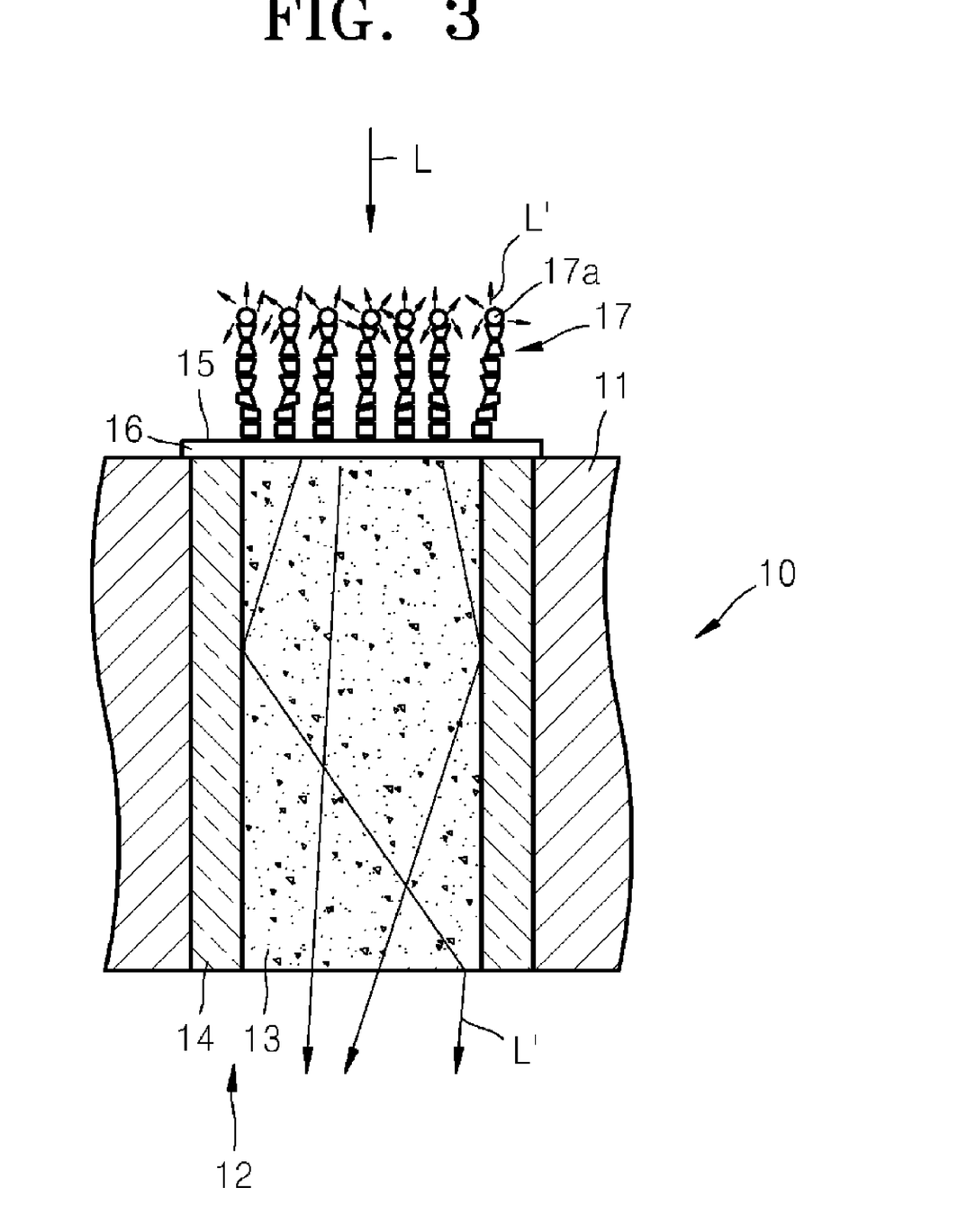
FIG. 3 is a partial cross-sectional view showing an optical path of fluorescent light in the integrated bio-chip of FIG. 1.

FIG. 1 is a perspective view of an integrated bio-chip (also referred to as a "biochip") according to an embodiment, FIG. 2 is a partial cross-sectional view of the integrated bio-chip of FIG. 1, and FIG. 3 is a partial cross-sectional view of an optical path of a fluorescent light beam emitted from a sample in the integrated bio-chip of an embodiment.

Referring to FIGS. 1 and 2, the integrated bio-chip 10 includes a substrate 11 and a plurality of excitation light absorbing waveguides 12. Each excitation light absorbing waveguide 12 of the plurality of excitation light absorbing waveguides 12 penetrates the substrate 11, as shown in FIG. 2. The excitation light absorbing waveguides 12 are integrated in the substrate 11, and samples are disposed on reaction regions 15 on the substrate 11. In an embodiment, the reaction regions 15 are not densely arranged on the substrate 11, as shown in FIG. 1.

The substrate 11 may be a semiconductor substrate, including silicon (Si), gallium arsenide (GaAs) or indium phosphide (InP), for example. In other embodiments, glass, a dielectric material, a metal material or a polymer may be used as the substrate 11.

The reaction regions 15, on which the samples are disposed, are arranged on a surface of the integrated bio-chip 10, such as an upper surface thereof (as viewed in FIG. 1). The reaction regions 15 are separated from each other, e.g., are spaced apart from each other, and correspond to the excitation light absorbing waveguides 12 in a one-to-one manner. The reaction regions 15 may be arranged in a two-dimensional array, such as in a substantially matrix pattern of columns and rows, for example.

An anti-reflection layer 16 is disposed on each of the reaction regions 15, as shown in FIGS. 1 and 2. The anti-reflection layer 16 prevents a fluorescent light beam, emitted from the sample, from being reflected. The anti-reflection layer 16 may be disposed to cover end portions of the excitation light absorbing waveguide 12 exposed above the upper surface of the substrate 11. In addition, the anti-reflection layer 16 may be formed from a material affinitive to the samples (or a liquid in which the samples are dispersed).

The anti-reflection layer 16 of the integrated bio-chip 10 may be omitted in other embodiments. When the anti-reflection layer 16 is omitted, the surfaces of the reaction regions 15 may be treated to have affinity to the samples (or to the liquid in which the samples are dispersed). The surface treatment may vary, depending on the sample that is to be detected. For example, when the substrate 11 is formed of a hydrophobic material, such as silicon, for example, the reaction regions 15 may be locally oxidized to have a hydrophilic property. However, the embodiments described herein are not limited to the surface treatment described above. Instead, various surface treatment methods, such as an ion exchange surface or an immobilized metal surface, for example, may be used, depending on the type of sample to be detected by the bio-chip 10.

In an embodiment, the samples disposed on the integrated bio-chip 10 may be detected using a fluorescence detection method. The samples may be, for example, bio-materials 17 (FIG. 3), such as a nucleotide having fluorescent tags. As described above, the reaction regions 15 are arranged in a predetermined pattern, and samples, such as the bio-materials, are disposed on, e.g., are attached to, the reaction regions 15. For example, when the integrated bio-chip 10 is used as a deoxyribonucleic acid ("DNA") chip, each of the reaction regions 15 becomes a minimum unit on which a plurality of probe nucleotides of a same kind are attached, and is a minimum pixel of a fluorescent image obtained when the excitation light is irradiated onto the DNA chip for detecting target nucleotides. Each of the reaction regions 15 may have a diameter in a range of about 0.1 micrometer (μm) to about 99 μm, and the reaction regions 15 may be arranged in the two-dimensional arrangement described above. In FIG. 1, the reaction region 15 has a substantially circular shape; however, the reaction region 15 may have other shapes, such as a polygonal shape, such as a rectangle, for example, but other embodiments are not limited thereto.

The excitation light absorbing waveguides 12 penetrate the substrate 11. An first end portion of each of the excitation light absorbing waveguides 12 is disposed on a surface of the substrate 11 (e.g., the upper surface of the substrate 11, as shown in FIGS. 1 and 2), to which the samples are attached, and a second end portion, opposite to the first end portion, of each of the excitation light absorbing waveguides 12 is disposed on an opposite surface of the substrate 11 (e.g., a lower surface thereof). The first end portion of the excitation light absorbing waveguide 12 disposed on the upper surface of the substrate 11 (to which the samples are attached) may coincide with the reaction region 15 to which the samples may be easily attached.

Each of the excitation light absorbing waveguides 12 includes a color filter core 13 and a clad layer 14, as shown in FIGS. 2 and 3.

The color filter core 13 is formed of a material that transmits the fluorescent light beam emitted from the sample and absorbs the excitation light that excites the sample, and a transverse cross-section of the color filter core 13 may be a circle or, alternatively, a polygon. The cross-sectional shape of the color filter core 13 may correspond to a shape of the reaction region 15. In an embodiment, a wavelength of the fluorescent light is longer than a wavelength of the excitation light, and thus, the color filter core 13 may be formed of a color filter material having a passband that is equal to the wavelength band of the fluorescent light. For example, a transparent semiconductor material, polymer or dielectric material may be dyed using a dye having a wavelength corresponding to a wavelength of the fluorescent light or, alternatively, the dye having the wavelength corresponding to the wavelength of the fluorescent light may be mixed with or dispersed in the transparent semiconductor material, the polymer, or the dielectric material.

The clad layer 14 is formed of a material having a refractive index that is lower than that of the color filter core 13 so as to totally reflect the fluorescent light passing through the color filter core 13. For example, the clad layer 14 may be formed of an oxide material such as magnesium dioxide ($MgO_2$) or silicon dioxide ($SiO_2$). In an embodiment, the refractive index of the clad layer 14 may be reduced by adding a dopant. In addition or alternatively, the refractive index of the color filter core 13 may be increased by adding the dopant to the color filter core 13.

The clad layer 14 may have a multi-layered structure, in which layers thereof have different refractive indexes from each other. In other embodiments, the clad layer 14 may have a structure having a refractive index that gradually changes. If the refractive index of the substrate 11 is smaller than the refractive index of the color filter core 13, the clad layer 14 may be omitted, and the substrate 11 around the color filter core 13 may be used as the clad layer. On the other hand, when the refractive index of the color filter core 13 is gradually changed, such as when a graded index optical fiber is used, for example, the refractive index may be changed at a boundary between the color filter core 13 and the clad layer 14.

Referring now to FIG. 3, samples, such as bio-materials 17, may be disposed on the reaction regions 15 of the integrated bio-chip 10. The bio-materials 17 disposed on the reaction regions 15 are biological receptors for target bio-materials. Specifically, for example, the bio-materials 17 on the reaction regions 15 are probe bio-materials that interact with target bio-materials that are to be detected. The probe bio-materials are molecules that may interact with the target bio-materials, such as via a hybridization of nucleotides or an antigen-antibody interaction, e.g., a nucleotide molecule having a sequence that is complementary to the nucleotide molecule that is to be detected. In another embodiment, the target bio-materials may be biological organic materials, such as enzymes of living creatures, protein, antibodies, nucleotides, microorganisms, cells and organs of animals and plants, or nerve cells, for example.

To detect the target bio-materials, the integrated bio-chip 10 uses a fluorescence detection method. Therefore, fluorescent materials 17a are tagged onto the bio-materials 17. The bio-materials 17, on which the fluorescent materials 17a are tagged, may be the probe bio-materials or the target bio-materials, depending on the type of the fluorescent mechanism of emitting fluorescent light L'. For example, the tagged fluorescent materials 17a may emit the fluorescent light L' due to excitation light L, or may be activated by an interaction between the probe bio-materials and the target bio-materials to emit the fluorescent light L' due to the excitation light L.

The surface of the integrated bio-chip 10, on which the bio-materials are attached, is treated (as described in greater detail above) and thus, the bio-materials are attached only to the reaction regions 15. On one reaction region 15, the bio-materials 17 of the same kind may be attached. The bio-materials 17 of different kinds may be attached to different reaction regions 15. The bio-materials 17 of the same kind may be attached to each of the reaction regions 15. The bio-materials 17, e.g., the probe bio-materials, are attached to the reaction regions 15 at predetermined locations using a bio-chemical process or a semiconductor process, for example.

In an exemplary embodiment using a DNA chip, probe nucleotides of a plurality of types of nucleotides are attached to predetermined reaction regions 15 from among the plurality of reaction regions 15 in single stranded shapes as the probe bio-materials. The probe nucleotides include a nucleotide having a sequence that is complementary to the sequence of the target nucleotide, such as messenger ribonucleic acid ("mRNA"), for example. When a liquid including the target nucleotides flows onto the surface of the DNA chip, the probe nucleotides, having sequences complementary to those of the target nucleotide, combine with the target nucleotides via a hybridization reaction, and the nucleotides that are not combined with the probe nucleotides of the DNA chip are washed off. The nucleotide that is hydrodized, e.g., that is combined with the target nucleotides via the hybridization reaction, emits the fluorescent light L' due to the fluorescent material tagged thereon, and thus, the integrated bio-chip 10 determines whether the target nucleotide exists by detecting a location from which the fluorescent light L' is emitted. Locations of the probe nucleotides are determined in advance, and thus, the existence of the plurality of target nucleotides may be determined from detected two-dimensional fluorescent images.

The fluorescent light L' is generated due to the excitation light L, and the fluorescent light L' proceeding downward (as viewed in FIG. 3) passes through the excitation light absorbing waveguide 12 and is emitted from the lower surface of the integrated bio-chip 10. On the other hand, the excitation light L also proceeds downward, however, the excitation light L is absorbed and blocked by the excitation light absorbing waveguide 12. As described in greater detail above, since only the fluorescent light L' is emitted from the lower surface of the integrated bio-chip 10, the integrated bio-chip 10 effectively determines whether the target bio-materials are detected from the fluorescent images at the lower surface of the integrated bio-chip 10.

Since the fluorescent light L' emitted due to the excitation light L is non-directional, the fluorescent light L' radiates in all directions. However, since the excitation light absorbing waveguide 12 has an optical fiber waveguide structure, when an incident angle of the fluorescent light L' exceeds a predetermined range, the light is not guided into the excitation light absorbing waveguide 12. Therefore, the fluorescent light L' is only guided through the excitation light absorbing waveguide 12 that is located under the reaction region 15, on which the bio-materials 17 emitting the above fluorescent light L' are disposed, and thus, any blurring of the fluorescent image due to the fluorescent light L' emitted from the neighboring bio-materials 17 is substantially reduced and/or is effectively prevented.

Figure 4:
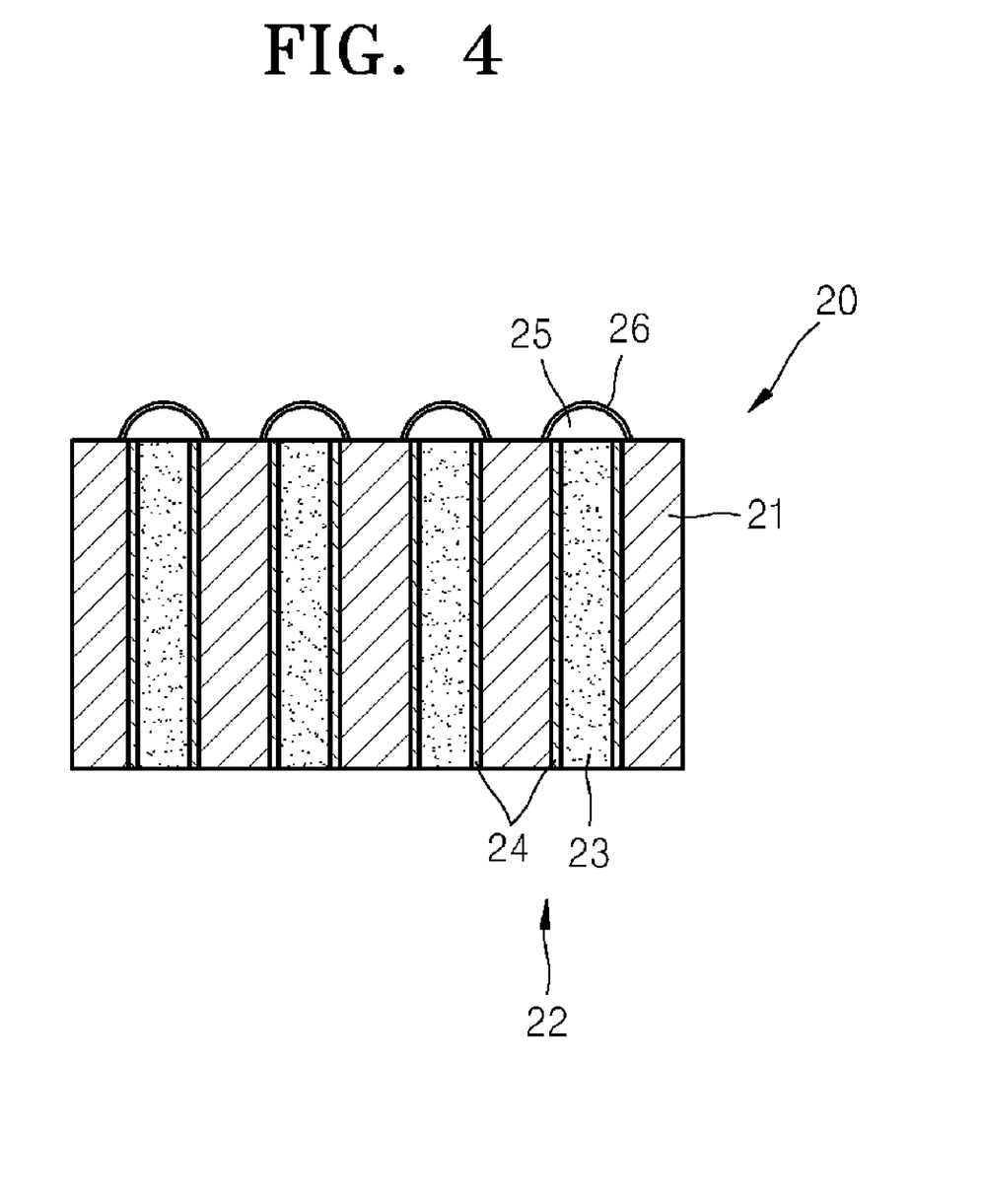
FIG. 4 is a partial cross-sectional view of an integrated bio-chip according to another embodiment.

FIG. 4 is a partial cross-sectional view of an integrated bio-chip 20 according to another embodiment. The integrated bio-chip 20 of another embodiment further includes a micro lens 25, in addition to the structures of the integrated bio-chip 10 described above.

Referring to FIG. 4, the integrated bio-chip 20 includes a substrate 21, a plurality of excitation light absorbing waveguides 22 penetrating the substrate 21, and a plurality of micro lenses 25 disposed on end portions of each excitation light absorbing waveguide 22 of the plurality of excitation light absorbing waveguides 22. Each of the excitation light absorbing waveguides 22 includes a color filter core 23 and a clad layer 24. The substrate 21 and the excitation light absorbing waveguides 22 are substantially the same as those described in greater detail above with reference to FIGS. 1 through 3, and any repetitive detailed description thereof will hereinafter be omitted.

The micro lenses 25 correspond to the end portions of the excitation light absorbing waveguides 22 in a one-to-one correspondence. A surface of the micro lens 25 is a reaction region to which samples are attached, and a peripheral portion of the micro lens 25 is a non-reaction region to which the samples are not attached. The surface of the micro lens 25 and/or the peripheral surface of the micro lens 25 are treated so that the samples are attached only to the surface of the micro lens 25. For example, when the substrate 21 is formed of a material that is not affinitive to the samples (or a liquid in which the samples are dispersed), the surface of the micro lens 25 may be treated to have an affinity to the samples (or to the liquid in which the samples are dispersed). The surface treatments described above may vary, depending on a type of samples that are to be detected. For example, when the substrate 21 is formed of a hydrophobic material, such as silicon, the micro lens 25 may be oxidized to have a hydrophilic property.

An anti-reflection layer 26 is disposed on the surface of the micro lens 25 to prevent loss of fluorescent light on the surface of the micro lens 25. As described in greater detail above, the anti-reflection layer 26 may be formed of a material that is affinitive to the samples (or to the liquid in which the samples are dispersed).

In an embodiment, the micro lens 25 has a convex shape, and has a refractive power to condense the fluorescent light emitted from the samples. Since the surface of the micro lens 25 is convex, the surface area of the micro lens 25 is wider than the plane surface area. The surface of the micro lens 25 becomes the reaction region to which the samples are attached, and thus, when the convex micro lens 25 is used, more samples may be attached than those attached to the plane surface. Therefore, an intensity of the fluorescent light emitted from the samples that are to be detected is increased.

In addition, the fluorescent light incident to the excitation light absorbing waveguide 22 may be transferred only when the fluorescent light satisfies the total internal reflection conditions in the excitation light absorbing waveguide 22. Therefore, an incident angle of the light that transferred through the excitation light absorbing waveguide 22 is determined. In an embodiment, since the fluorescent light incident to the excitation light absorbing waveguide 22 is refracted by the micro lens 25, the tilted incident fluorescent light may be transferred while satisfying the total reflection conditions of the excitation light absorbing waveguide 22. Accordingly, a maximized amount of the fluorescent light emitted from the samples is transferred through the excitation light absorbing waveguide 22 of the integrated bio-chip 20.

On the other hand, when the fluorescent light exits the excitation light absorbing waveguide 22 (after transferring through the excitation light absorbing waveguide 22), a cross-sectional area of the light flux increases gradually. As used herein, Rayleigh length indicates a length from a point where the cross-sectional area of the light flux is minimum to a point where the cross-sectional area of the light flux becomes twice the minimum value. Therefore, a photodetector (not shown) may be disposed on a portion that is spaced apart from the end portions of the excitation light absorbing waveguides 22 at about one Rayleigh length, to further improve the efficiency of detecting the fluorescent light.

In an embodiment, the micro lens 25 is formed as a convex hemisphere, however, the shape of the micro lens is not limited to the foregoing description.

Figure 5:
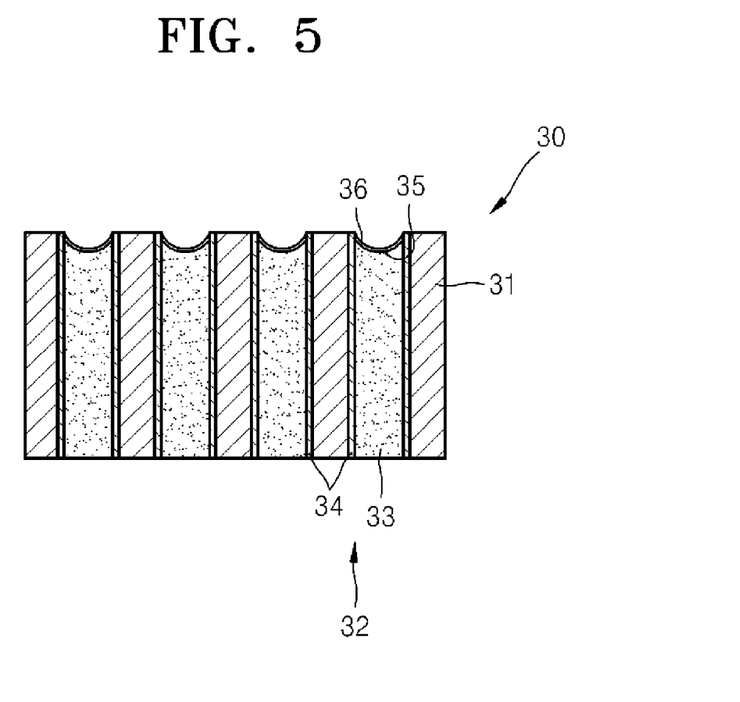
FIG. 5 is a partial cross-sectional view of an integrated bio-chip according to another embodiment.

FIG. 5 is a partial cross-sectional view that shows an integrated bio-chip 30 having micro lenses which are formed as concave hemispheres. In the embodiment shown in FIG. 5, it will be assumed for purposes of description herein that the refractive index of the micro lens 25 (described above with reference to FIG. 4) is greater than that of the outer portion. However, since the samples, such as the target bio-materials, for example, flow along the surface of the integrated bio-chip 30 when they are dispersed in a liquid, the refractive index of the liquid in which the samples are dispersed may be greater than that of the micro lens 25.

Specifically, in the integrated bio-chip 30 shown in FIG. 5, a plurality of micro lenses 35 having concave hemispherical shapes are disposed on the surface of the substrate 31 when the refractive index of the liquid in which the samples are dispersed is greater than that of excitation light absorbing waveguides 32. An anti-reflection layer 36 is disposed on the surface of each of the micro lenses 35 to prevent loss of fluorescent light on the surface of the micro lens 35. As described in further detail above, the anti-reflection layer 36 may be formed of a material that is affinitive to the samples (or to the liquid in which the samples are dispersed).

Figure 6:
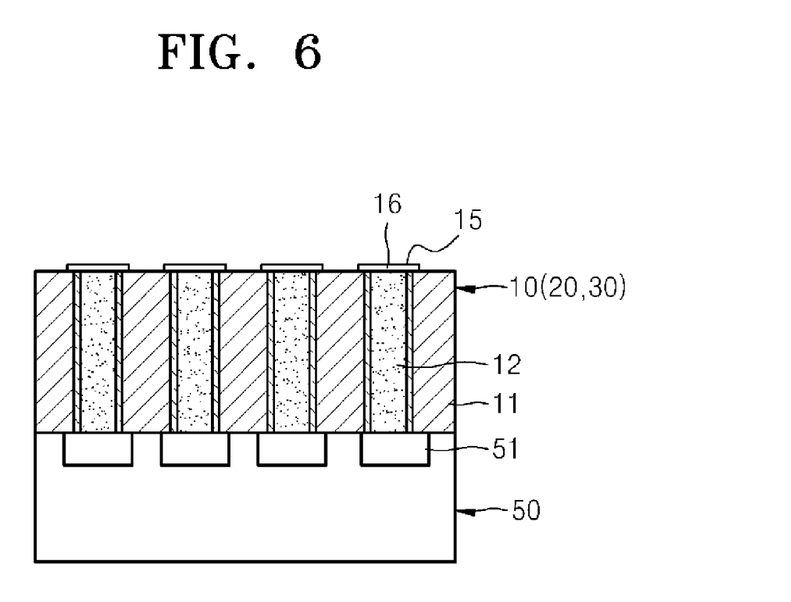
FIG. 6 is a partial cross-sectional view illustrating alignment of the integrated bio-chip and a photodetector according to one or more embodiments.

FIG. 6 is a partial cross-sectional view illustrating an arrangement of the integrated bio-chip 10, 20 or 30 and a photodetector according to an embodiment.

A photodetector 50 may be an image sensor such as a photomultiplier tube ("PMT"), a charge coupled device ("CCD"), a complementary metal oxide semiconductor ("CMOS") image sensor ("CIS"), or a scanner using one of the above-listed image sensors.

As described in greater detail above, the fluorescent light emitted from the samples, such as the bio-materials, attached to the upper surface of the substrate 11 is emitted from the lower surface of the substrate 11 through the excitation light absorbing waveguides 12. Thereafter, the fluorescent light emitted from the end portions of the excitation light absorbing waveguides 12 at on the lower surface of the substrate 11 is condensed at a point apart from the lower surface of the substrate 11 at about one Rayleigh length. Therefore, the photodetector 50 may be disposed in contact with the integrated bio-chip 30 (or the integrated bio-chips 10 and 20 described above), or may be disposed within about one Rayleigh length thereof to further improve the efficiency of detecting the fluorescent light.

In one embodiment, an end of the excitation light absorbing waveguide 12 contacts the reaction region 15 of the substrate 11, and the other end of the excitation light absorbing waveguide 12 is exposed on the lower surface of the substrate 11. Therefore, the lower surface of the substrate 11 has patterns that correspond to the reaction regions 15 in one-to-one correspondence. Thus, the image formed by the fluorescent light beams emitted from the reaction regions 15 of the substrate 11 is displayed on the lower surface of the substrate 11. One or more pixels 51 in the photodetector 50 are disposed to correspond to each reaction region 15 of the substrate 11. Thus, the pixels 51 of the photodetector 50 are disposed to correspond to the end portions of the excitation light absorbing waveguides 12 exposed on the lower surface of the substrate 11 in a one-to-one correspondence (or, alternatively, in a one-to-many correspondence), and thus, the fluorescent images emitted from the plurality of reaction regions 15 may be read without requiring an additional optical member.

As described above, since the fluorescent images may be read directly by the photodetector 50 disposed adjacent to the integrated bio-chip 10, 20 or 30, the photodetector 50 using the integrated bio-chip 10, 20 or 30 according to one or more embodiments does not require an optical detecting system, thereby substantially reducing manufacturing costs. In addition, a size of the photodetector 50 is minimized.

The embodiments described above with reference to FIGS. 1 through 6 illustrate the integrated bio-chip 10, 20 or 30 that includes the plurality of excitation light absorbing waveguides 12, 22 or 32 and the plurality of reaction regions 15 or 35, but it will be noted that additional embodiments are not limited thereto. For example, in another embodiment, the integrated bio-chip includes a single excitation light absorbing waveguide and a single reaction region.

FIGS. 7A through 7E are partial cross-sectional views illustrating processes of fabricating an integrated bio-chip according to an embodiment.

Figure 7A:
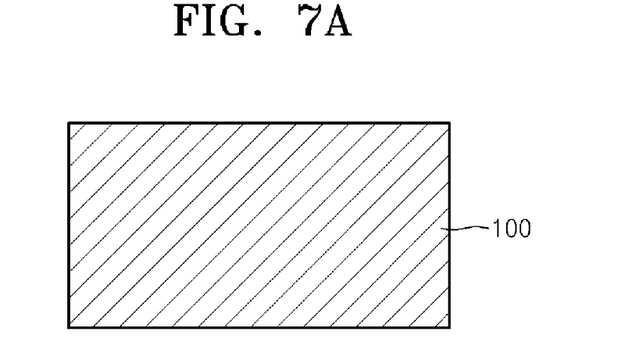
FIGS. 7A through 7E are partial cross-sectional views illustrating processes of fabricating an integrated bio-chip according to an embodiment.

Referring to FIG. 7A, a substrate 100 is prepared. The substrate 100 may be formed of a glass material, a semiconductor material, a metal material, a dielectric material or a polymer, for example. The substrate 100 may be formed of a material that is not affinitive to samples (or to a liquid in which the samples are dispersed). For example, the substrate 100 may be a silicon substrate having a hydrophobic property. A surface of the substrate 100 may be formed as a planarized layer or may be planarized using a chemical mechanical polishing ("CMP") process.

Figure 7B:
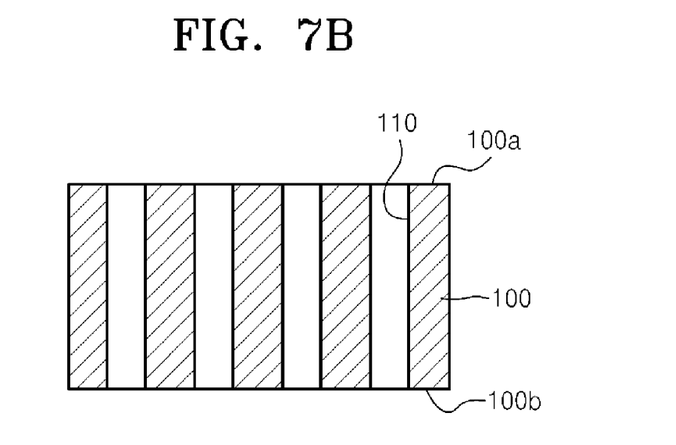

Referring to FIG. 7B, a plurality of penetration holes 110 is formed in the substrate 100. A diameter of each penetration hole 110 of the plurality of the penetration holes 110 may be in a range of about 0.1 μm to 99 μm. The penetration holes 110 may be formed using a through silicon via ("TSV") process, for example.

When the diameter of the penetration hole 110 is relatively small, the penetration hole 110 may not penetrate through the substrate 100. In this case, a bottom surface 100b, opposite to a surface 100a where the penetration hole 110 is formed, may be polished to be deeper than a length of the penetration hole 110 (e.g., a back-lap process) so that the penetration hole 110 penetrates the substrate 100. The back-lap process may be performed after forming excitation light absorbing waveguides (described below) or, alternatively, after processing the surface of the substrate.

Figure 7C:
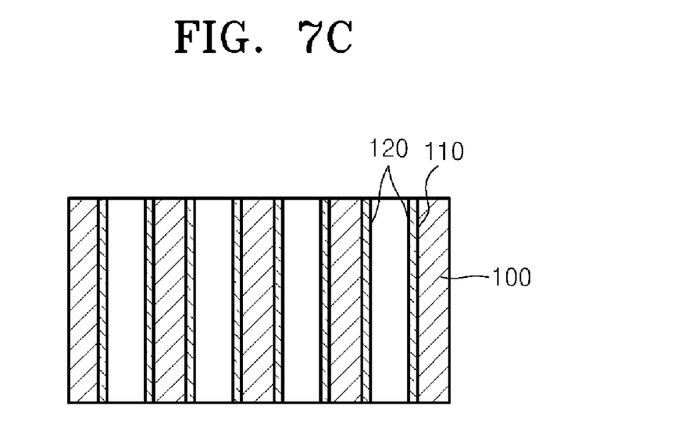

Referring to FIG. 7C, an inner wall surface of the penetration hole 110 in the substrate 100 is oxidized to lower a refractive index thereof, and a clad layer 120 is formed thereon. The refractive index may be adjusted by controlling the oxidization level and/or by adding a dopant. The clad layer 120 may be formed by injecting the dopant in the penetration hole 110 to disperse the dopant to the inner wall surface of the penetration hole 110, or by applying a material having a low refractive index to the inner wall surface of the penetration hole 110.

Figure 7D:
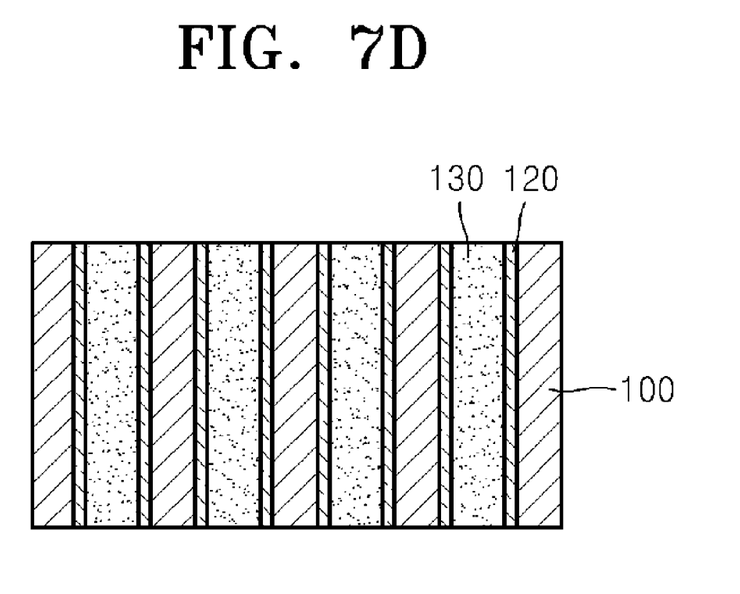

Referring to FIG. 7D, a color filter material is filled in the penetration hole 110, in which the clad layer 120 is formed, in order to form a color filter core 130. The color filter material is combined with a dye or a pigment, absorbs excitation light having fluorescent wavelength band using a transparent binder, and has a refractive index that is greater than that of the clad layer 120. After filling the color filter material, the surface of the substrate 100 may be planarized using the CMP process, for example.

Figure 7E:
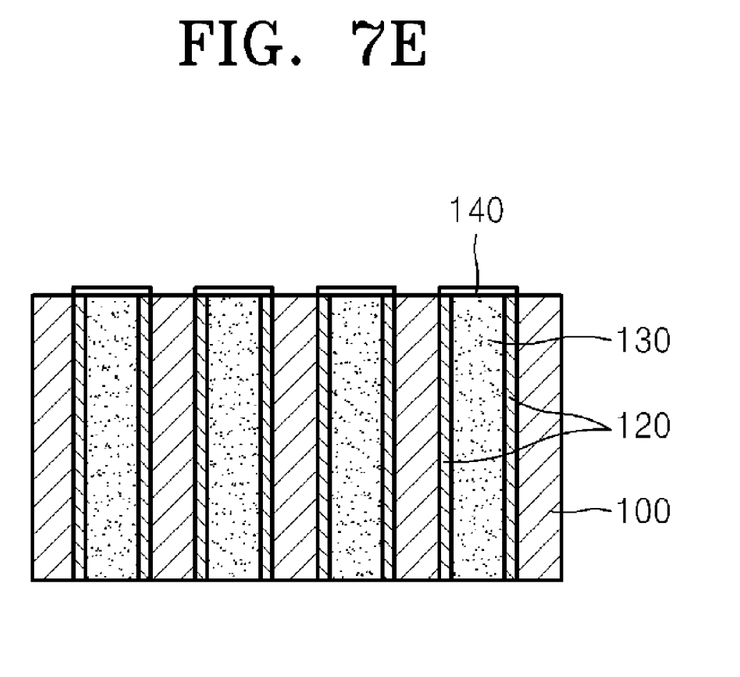

Referring to FIG. 7E, an anti-reflection layer 140 is formed on exposed portions of the clad layer 120 and the color filter core 130 on the substrate 100. The anti-reflection layer 140 may be formed using a photolithography process, for example.

Instead of forming the anti-reflection layer 140, the exposed portions of the clad layer 120 and the color filter core 130 on the substrate 100 may be treated to increase an affinity thereof to samples (or to a liquid in which the samples are included). In an embodiment, a process of forming a micro lens on the exposed portions of the clad layer 120 and the color filter core 130 on the substrate may be performed before forming the anti-reflection layer 140. The micro lens may be formed by forming pillar shapes of patterns corresponding to micro lenses, using a photoresist, and transforming the pillar shapes of the photoresist patterns to curved shapes using a reflow process.

As described above, when the depth of the penetration hole 110 is not large enough to penetrate through the substrate 100, the thickness of the substrate 100 may be reduced through the back-lap process, e.g., polishing the bottom surface of the substrate 100, and thus, the end portions of the clad layer 120 and the color filter core 130 are exposed at the surface of the substrate 100.

Bio-materials may be disposed on, e.g., attached to, the integrated bio-chip fabricated through the above described processes. For example, DNA bases such as adenine ("A"), guanine ("G"), cytosine ("C"), and thymine ("T") are stacked on the micro lenses in different sequences, and thus, a DNA chip having probe DNAs with predetermined sequences is fabricated.

Hereinafter, a bio-materials detecting apparatus using the integrated bio-chip according to the embodiments described will be described in further detail with reference to FIGS. 8 and 9.

Figure 8:
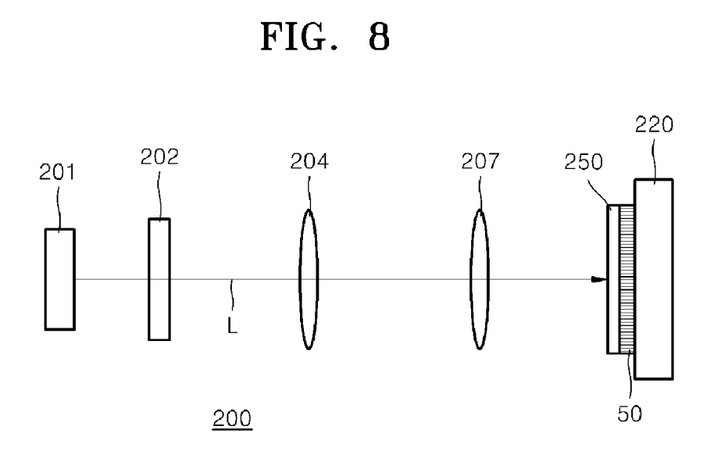
FIG. 8 is a block diagram of an apparatus for detecting bio-materials according to an embodiment.

FIG. 8 is a block diagram of a bio-materials detecting apparatus 200 according to an embodiment.

Referring now to FIG. 8, the bio-materials detecting apparatus 200 includes a light source 201, e.g., an illuminating optical system which irradiates, e.g., emits, excitation light L onto an integrated bio-chip 250, a light diffusing device 202, a collimating lens 204 and a condensing lens 207. The integrated bio-chip 250 and the photodetector 50 are installed on a stage 200.

Specifically, the photodetector 50 may be fixedly installed on the stage 220, or may be detachably installed on the stage 220. However, the integrated bio-chip 250 is detachably installed on the stage 220. The integrated bio-chip 250 may be installed on the stage 220 by being contacted to the photodetector 50 or by being placed adjacent to the photodetector 50 at about one Rayleigh length from the photodetector 50, but alternative embodiments are not limited thereto.

The light source 201 emits the excitation light L. The excitation light L excites fluorescent materials attached to the bio-materials in the integrated bio-chip 250. In an embodiment, light having a wavelength of about 500 nanometers (nm) is used as the excitation light L, however, the wavelength of the excitation light L may be different, based on the fluorescent materials tagged on the bio-materials.

The light diffusing device 202 diffuses the excitation light L evenly, and the excitation light L therefore has a substantially even intensity throughout the entire cross section of, for example, a bar type light integrator or a micro-patterned substrate. The excitation light L has uniform intensity throughout the entire cross section thereof, and light with a substantially constant intensity is thereby irradiated onto some regions or, alternatively, the entire region of the integrated bio-chip 350.

The collimating lens 204 changes the excitation light L into parallel light. In an embodiment shown in FIG. 8, the collimating lens 204 is disposed between the light diffusing device 202 and the condensing lens 207. However, in other embodiments, the collimating lens 204 may be disposed between the light source 201 and the light diffusing device 202. In yet another in which the excitation light L emitted from the light source 201 does not substantially diverge, and the condensing lens 207 thereby sufficiently condenses the excitation light L, the collimating lens 204 may not be used.

The condensing lens 207 condenses the excitation light L so that a light spot having a predetermined diameter is formed on the integrated bio-chip 250. The diameter of the light spot may cover a part of the integrated bio-chip 250 or, alternatively, the entire region of the integrated bio-chip 250.

The photodetector 50 reads fluorescent images formed on the lower surface of the integrated bio-chip 250. The photodetector may be, for example, an image sensor such as a PMT, a CCD or a CIS, as described above.

The integrated bio-chip 250 may be attached to the photodetector 50. The photodetector 50 may be disposed so that pixels (not shown) thereof correspond to reaction regions 15 (FIG. 1) in the integrated bio-chip 250 in a one-to-one correspondence or, alternatively, in a one-to-many correspondence. Accordingly, an additional detecting optical system for scanning is not required, and the photodetector 50 according to an embodiment reads the fluorescent images emitted from the integrated bio-chip 250. As a result, the bio-materials detecting apparatus 200 only requires the illuminating optical system, and thus, may be fabricated to be a portable unit. In addition, the samples, such as the bio-materials, may be analyzed and detected without regard to a geographic location, e.g., outside of a laboratory.

When the light spot of the excitation light L covers the entire surface of the integrated bio-chip 250, the photodetector 50 simultaneously detects all of the fluorescent images emitted from the integrated bio-chip 250. On the other hand, when the light spot of the excitation light L covers only a part of the integrated bio-chip 250, the stage 220 or the illuminating optical system moves to cover the entire surface of the integrated bio-chip 250 in a sequential order. In addition, the photodetector 50 may obtain the fluorescent images of the entire area of the integrated bio-chip by combining the fluorescent images emitted from the integrated bio-chip 250 in the sequential order.

Figure 9:
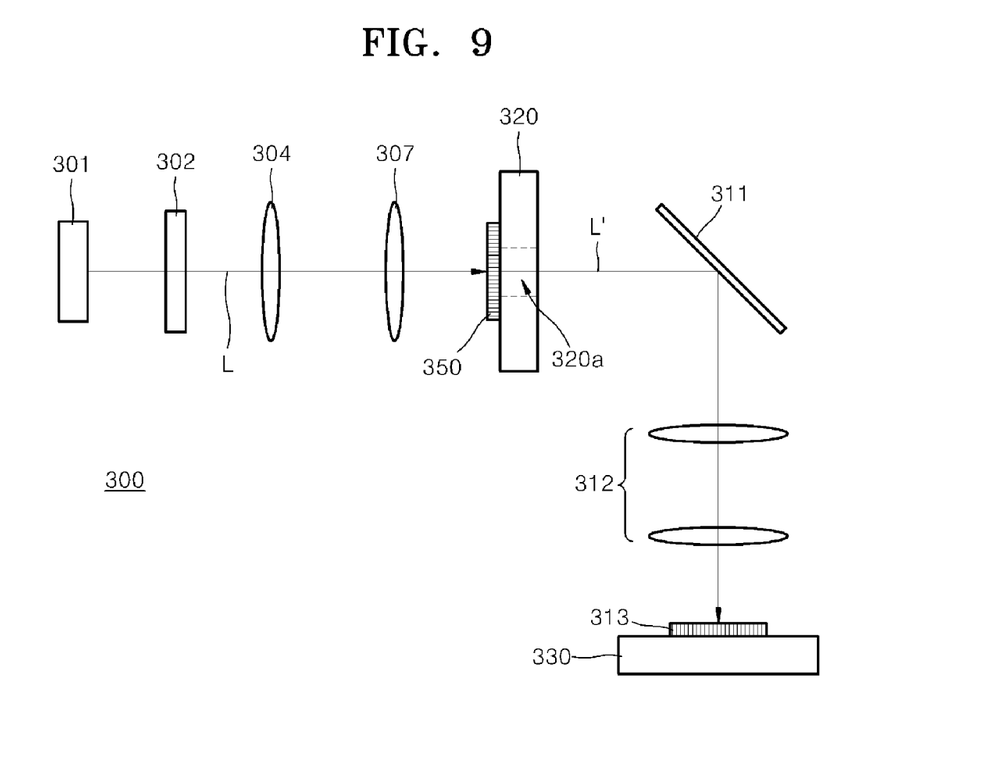
FIG. 9 is a block diagram of apparatus for detecting bio-materials according to another embodiment.

FIG. 9 is a block diagram of a bio-materials detecting apparatus 300 according to another embodiment.

Referring to FIG. 9, the bio-materials detecting apparatus 300 includes a light source 301, e.g., an illuminating optical system which irradiates, e.g., emits, excitation light L onto an integrated bio-chip 350, a light diffusing device 302, a collimating lens 304 and a condensing lens 307. In addition, the bio-materials detecting apparatus 300 includes a projection optical system 312, e.g., an optical detecting system for transferring fluorescent lights emitted from the integrated bio-chip 350 to a photodetector 313. Reference numeral 311 denotes a mirror for folding an optical path, reference numeral 320 denotes a first stage on which the integrated bio-chip 350 is mounted, and reference numeral 330 denotes a second stage on which the photodetector 313 is disposed.

The integrated bio-chip 350 used in the bio-materials detecting apparatus 300 shown in FIG. 9 may be one of the integrated bio-chips 10, 20 or 30, described in greater detail above with reference to FIGS. 1-5, and the photodetector 313 is formed independently from the integrated bio-chip 350.

The light source 301, the light diffusing device 302, the collimating lens 304, and the condensing lens 307 are substantially the same as the corresponding components in the bio-materials detecting apparatus 200 described in greater detail above with reference to FIG. 8, and thus, any repetitive detailed description thereof will hereinafter be omitted.

The integrated bio-chip 350 is mounted on the first stage 320 to be detachable, and fluorescent light L', emitted due to the excitation light L, proceeds toward a lower surface of the integrated bio-chip 350 through a window 320a in the first stage 320.

The projection optical system 312 and the photodetector 313 are disposed on a side of the lower surface of the integrated bio-chip 350. The integrated bio-chip 350 includes excitation light absorbing waveguides (described in greater detail above) and, thus, the fluorescent light L' is emitted only from the lower surface of the integrated bio-chip 350.

The projection optical system 312 projects the fluorescent images, emitted from the lower surface of the integrated bio-chip 350, to the photodetector 313 and, in an exemplary embodiment, may be a lens system including a plurality of lenses, for example.

The photodetector 313 reads the fluorescent images formed on the lower surface of the integrated bio-chip 350, and may be, for example, an image sensor such as the PMT, the CCD or the CIS (described above). In another embodiment, a scanner, including one of the above-listed image sensors, and a scanning driver may be used as the photodetector 313.

When a light spot of the excitation light L covers the entire surface of the integrated bio-chip 350, the photodetector 313 may simultaneously detect all fluorescent images emitted from the integrated bio-chip 350. In contrast, when the light spot of the excitation light L covers only a part of the integrated bio-chip 350, the first stage 320 or the illuminating optical system may move so that the excitation light L may cover the entire surface of the integrated bio-chip 350 in a sequential manner. In addition, the photodetector 313 combines the fluorescent images sequentially emitted from the integrated bio-chip 350 to obtain the fluorescent image of the entire integrated bio-chip 350.

In the embodiments described above, the illuminating optical system or the projection optical system is a refractive optical system including lenses. However, additional or alternative embodiments are not limited thereto. For example, the optical systems may be reflective optical systems including concave mirrors and/or convex mirrors. In addition, an arrangement and order of the optical members in the optical system may be changed, and some elements may be omitted.

It will be understood that the embodiments described herein should be considered in a descriptive sense only and not for purposes of limitation. Descriptions of aspects within each embodiment should be considered as available for other similar aspects in other embodiments.

Similarly, general inventive concept should not be construed as being limited to the embodiments set forth herein.

Rather, these embodiments are provided so that this disclosure will be thorough and complete and will fully convey the general inventive concept to those skilled in the art.

Thus, while the general inventive concept has been particularly shown and described with reference to embodiments thereof, it will be understood by those of ordinary skill in the art that various changes in form and details may be made therein without departing from the spirit or scope of the general inventive concept as defined by the following claims

What is claimed is:

1. An integrated bio-chip comprising:
   a substrate including one or more reaction regions on which samples are disposed; and
   one or more excitation light absorbing waveguides disposed in the substrate, wherein
   a first end portion of each of the one or more excitation light absorbing waveguides is exposed from the substrate at an upper surface thereof,
   a second end portion of each of the one or more excitation light absorbing waveguides is exposed from the substrate at a lower surface thereof,
   the one or more reaction regions are disposed at the upper surface of the substrate, and
   each of the one or more excitation light absorbing waveguides includes a color filter core which transmits fluorescent light emitted from the samples and absorbs excitation light which excites the samples,
   wherein each of the one or more excitation light absorbing waveguides is disposed in a through hole in the substrate that extends from the upper surface to the lower surface, and
   wherein the upper and lower surfaces define opposite major surface planes defining the substrate.

2. The integrated bio-chip of claim 1, wherein a refractive index of the color filter core is greater than a refractive index of the substrate surrounding the color filter core.

3. The integrated bio-chip of claim 1, wherein
   each of the one or more excitation light absorbing waveguides further includes a clad layer disposed around the color filter core, and
   a refractive index of the clad layer is less than a refractive index of the color filter core.

4. The integrated bio-chip of claim 1, wherein a shape of a transverse cross-section of the color filter core is one of a circle and a polygon.

5. The integrated bio-chip of claim 1, wherein surfaces of the one or more reaction regions are treated to attach the samples thereto.

6. The integrated bio-chip of claim 5, wherein
   the surfaces of the one or more reaction regions have hydrophilic properties, and
   non-reaction regions surrounding the surfaces of the one or more reaction regions have hydrophobic properties.

7. The integrated bio-chip of claim 1, further comprising one or more micro lenses disposed on the one or more reaction regions, wherein the one or more micro lenses condense the fluorescent light emitted from the samples.

8. The integrated bio-chip of claim 1, further comprising one or more micro lenses disposed on the one or more reaction regions, wherein the one or more micro lenses is a concave lens.

9. The integrated bio-chip of claim 7, wherein the one or more micro lenses is a convex lens.

10. The integrated bio-chip of claim 1, further comprising one or more anti-reflection layers disposed on the one or more reaction regions, wherein the one or more anti-reflection layers transmit the fluorescent light emitted from the samples.

11. The integrated bio-chip of claim 1, further comprising a photodetector disposed at the lower surface of the substrate, wherein the lower surface of the substrate is opposite to the upper surface of the substrate on which the one or more reaction regions is disposed.

12. The integrated bio-chip of claim 11, wherein the photodetector is disposed one of spaced apart from and adjacent to the substrate and in contact with the substrate.

13. The integrated bio-chip of claim 11, wherein pixels of the photodetector correspond to the one or more reaction regions in one of a one-to-one correspondence and a one-to-many correspondence.

14. The integrated bio-chip of claim 11, wherein the photodetector includes one of a photomultiplier tube, a charge coupled device and a complementary metal oxide semiconductor image sensor.

15. A method of fabricating an integrated bio-chip, the method comprising:
    forming one or more penetration holes in a substrate;
    forming one or more excitation light absorbing waveguides in the one or more penetration holes; wherein
    a first end portion of each of the one or more excitation light absorbing waveguides is exposed from the substrate at an upper surface thereof,
    a second end portion of each of the one or more excitation light absorbing waveguides is exposed from the substrate at a lower surface thereof, and
    each of the one or more excitation light absorbing waveguides includes a color filter core which transmits fluorescent light emitted from the samples and absorbs excitation light which excites the samples, and
    treating the upper surface of the substrate in which the one or more penetration holes are formed such that samples are attachable to reaction regions at which the one or more excitation light absorbing waveguides are formed,
    wherein the upper and lower surfaces define opposite major surface planes defining the substrate.

16. The method of claim 15, wherein
    the one or more penetration holes are through vias formed in the substrate, and
    the substrate comprises one of a semiconductor material, a dielectric material, a metal material and a polymer material.

17. The method of claim 15, wherein the forming the one or more excitation light absorbing waveguides comprises forming a color filter core by disposing a color filter material in each of the one or more penetration holes.

18. The method of claim 17, wherein the forming the one or more excitation light absorbing waveguides further comprises forming a clad layer on an inner wall of each of the one or more penetration holes.

19. The method of claim 18, wherein the forming the clad layer includes oxidizing the inner wall of each of the one or more penetration holes to reduce a refractive index of the inner wall of each of the one or more penetration holes.

20. The method of claim 18, wherein the forming the clad layer includes diffusing a dopant onto the inner wall of each of the one or more penetration holes to reduce a refractive index of the inner wall of each of the one or more penetration holes.

21. The method of claim 18, wherein the forming the clad layer includes applying a material having a refractive index which is less than a refractive index of a color filter core to the inner wall of each of the one or more penetration holes.

22. The method of claim 15, wherein the treating the surface of the substrate includes treating portions of the substrate at which the one or more excitation light absorbing waveguides are formed such that the portions have a hydrophilic property.

23. The method of claim 15, further comprising forming an anti-reflection layer on portions of the substrate adjacent to the reaction regions.

24. The method of claim 15, further comprising forming one or more micro lenses on portions of the substrate at which the one or more excitation light absorbing waveguides are formed.

25. The method of claim 15, further comprising performing a back-lap process to polish a lower surface of the substrate to a depth which is greater than a length of the one or more penetration holes.

26. An apparatus for detecting bio-material using an integrated bio-chip comprising a substrate including one or more reaction regions on which samples are disposed and one or more excitation light absorbing waveguides disposed in the substrate, the apparatus comprising:
   an illuminating optical system which irradiates excitation light onto the integrated bio-chip;
   a stage detachably mounted to the integrated bio-chip; and
   a photodetector which detects fluorescent light emitted from the integrated bio-chip, wherein
   a first end portion of each of the one or more excitation light absorbing waveguides is exposed from the substrate at an upper surface thereof,
   a second end portion of each of the one or more excitation light absorbing waveguides is exposed from the substrate at a lower surface thereof,
   the one or more reaction regions are disposed at the upper surface of the substrate, and
   each of the one or more excitation light absorbing waveguides includes a color filter core which transmits fluorescent light emitted from the samples and absorbs excitation light which excites the samples,
   wherein each of the one or more excitation light absorbing waveguides is disposed in a through hole in the substrate that extends from the upper surface to the lower surface, and
   wherein the upper and lower surfaces define opposite major surface planes defining the substrate.

27. The apparatus of claim 26, wherein the photodetector is disposed on the stage.

28. The apparatus of claim 27, wherein the photodetector is disposed one of spaced apart from and adjacent to the integrated bio-chip and in contact with the integrated bio-chip.

29. The apparatus of claim 26, further comprising a detecting optical system which transfers the fluorescent light emitted from the integrated bio-chip to the photodetector.

30. The apparatus of claim 26, wherein pixels of the photodetector correspond to the one or more reaction regions in one of a one-to-one correspondence and a one-to-many correspondence.

31. The apparatus of claim 26, wherein the photodetector includes one of a photomultiplier tube, a charge coupled device and a complementary metal oxide semiconductor image sensor.

* * * * *